US006821122B1

United States Patent
Wintermantel

(10) Patent No.: US 6,821,122 B1
(45) Date of Patent: Nov. 23, 2004

(54) JOINING ELEMENT FOR FASTENING DETACHABLE TOOTH PROSTHESES TO TOOTH CROWNS OR TO TOOTH IMPLANTS

(75) Inventor: Stefan Wintermantel, Mossingen (DE)

(73) Assignee: ZL Microdent - Attachment GmbH & Co KG., Breckerfeld (DE)

( * ) Notice: Subject to any disclaimer, the term of this patent is extended or adjusted under 35 U.S.C. 154(b) by 0 days.

(21) Appl. No.: 09/806,085
(22) PCT Filed: Jul. 22, 2000
(86) PCT No.: PCT/DE00/02387
§ 371 (c)(1),
(2), (4) Date: Mar. 22, 2001
(87) PCT Pub. No.: WO01/08589
PCT Pub. Date: Feb. 8, 2001

(30) Foreign Application Priority Data

Jul. 31, 1999 (DE) .......................... 199 36 121

(51) Int. Cl.[7] .............................. A61C 13/12
(52) U.S. Cl. ...................... 433/177; 433/181
(58) Field of Search .............. 433/177, 178, 433/181, 182, 183

(56) References Cited

U.S. PATENT DOCUMENTS 4,345,901 A * 8/1982 Romagnoli ................. 433/172
4,661,069 A * 4/1987 Weissman ................... 433/183
4,698,020 A * 10/1987 Menicacci .................. 433/177
4,850,869 A * 7/1989 Steinfort et al. ............ 433/172
5,120,222 A * 6/1992 Sulc ........................... 433/181

FOREIGN PATENT DOCUMENTS

DE   3720623   3/1983   ......... H61C/13/273
DE   4423768   5/1995
DE   1972863   1/1999

* cited by examiner

Primary Examiner—John J Wilson
(74) Attorney, Agent, or Firm—Horst M. Kasper

(57) ABSTRACT

A connection element for attachment of the movable dentures at tooth crowns or at tooth implants with a locking bolt (R) shiftable supported perpendicular to the pullout direction of the denture, wherein the locking bar (R) with its parts effective for the locking is guidable by the force of one or several springs (F) as seen from the pullout section of the denture under regions of one fixedly seated element (S) formed at one or several tooth crowns or, respectively, one or several tooth implants and wherein the locking element is again removable out of these regions by actuation of a pushbutton (D) acting onto the locking bar (R) with the parts of the locking bar effective for the locking and against this spring force, wherein a locking device (A) is furnished for the locking bar.

13 Claims, 4 Drawing Sheets

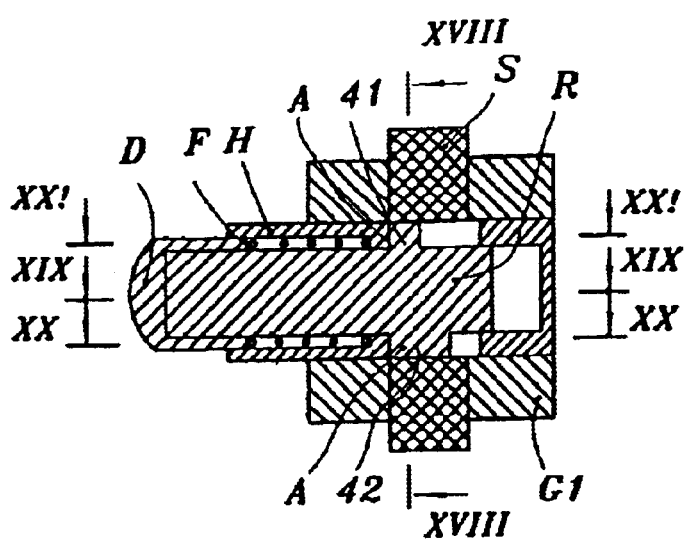
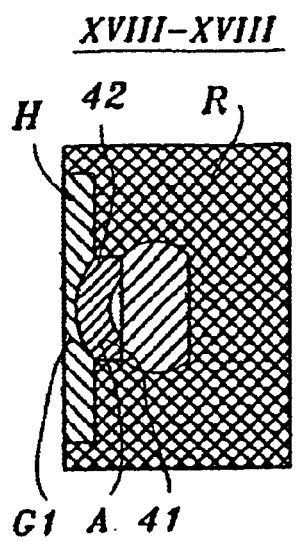
*Fig. 17*  *Fig. 18*
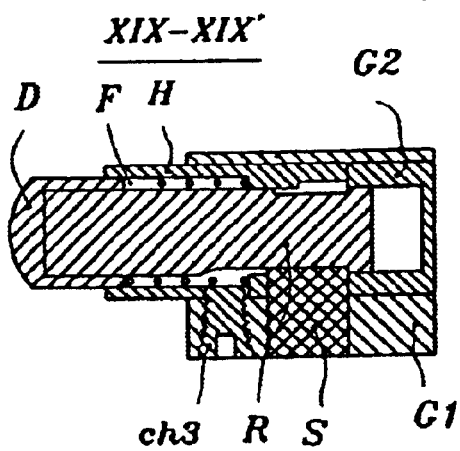
*Fig. 19*
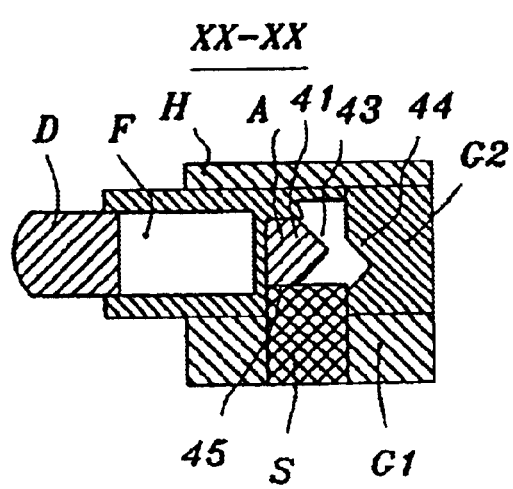
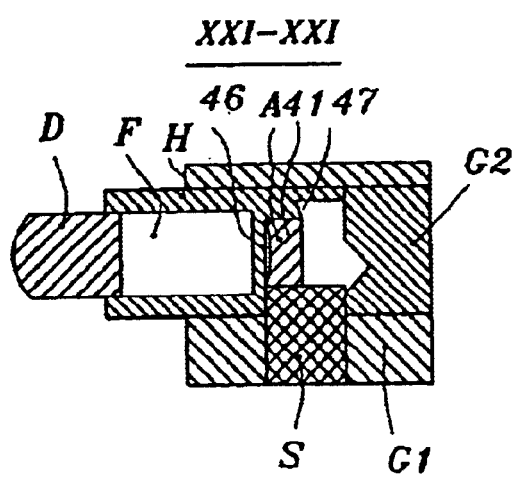
*Fig. 20*  *Fig. 21*

JOINING ELEMENT FOR FASTENING DETACHABLE TOOTH PROSTHESES TO TOOTH CROWNS OR TO TOOTH IMPLANTS

BACKGROUND OF THE INVENTION

1. Field of the Invention

The invention relates to a connection element for attaching of removable dentures at tooth crowns or tooth implants with the locking bar supported slidable perpendicular to the pullout direction of the denture, wherein the locking bar with its effective parts for the locking is guidable under regions of a fixedly positioned element formed at one or several tooth crowns or, to respectively, one or several tooth implants by the force of one or several springs as seen from the pullout direction of the denture and the locking bar is removable again from these regions by actuating of a pushbutton operating onto the locking bar with its parts effective for the bolting against this spring force.

2. Brief Description of the Background of the Invention Including Prior Art

Either active or passive connection elements are employed for attaching removable dentures at crowned teeth or tooth implants. In case of active elements the denture is connected to the tooth crown or the tooth implant by frictional engagement or by locking. The frictional force or the spring force has to be overcome in case of a removal of the denture. The active connection elements are associated with the disadvantage that the frictional force based on the wear for the spring force based on the spring fatigue can decrease in the course of time such that the attachment of the denture is not any longer assured. In addition, periodontal weak residual teeth or implants can be damaged in case the pull-out force of the denture is not precisely defined. Passive connection elements avoid the disadvantages. Here the support of the denture is accomplished by a pure shape matching with the locking bar device.

According to the state-of-the-art today in most cases still the conventional dental technological locking bars—hasp, sliding bolt and plug bar or, respectively, dead bolt are employed. The opening of the locking bars is performed in most cases by having the patient grip into a groove with a fingernail. The manual skill required for this however is not present with each patient. As special shape of a dead bolt represents a conventional construction, wherein the opening of the bolt is performed with a key, wherein the key is entered into a bore hole provided for this purpose.

For alleviation of the handling there have been proposed also so-called semi automatic locking bars, wherein the locking bar is opened by actuating of a pushbutton against the force of a spring. Such a semi automatic locking bar is described for example in the German printed patent document DE 3720623 A1. These semi automatic locking bars however are associated with the disadvantage that the pushbutton has to remain pressed down, which again can cause manual difficulties.

There are also so-called fully automatic locking bars known, which further alleviate the operation. In the known constructions of such locking bars, a locking element acting perpendicular to the direction of motion of the locking bar and formed as a leaf spring or as a spring plate loaded with an additional helical spring engages into a recess at the cylindrically shape locking bar axis from the closing direction after operating of the spring loaded pushbutton and retains the locking bar axis such that the pushbutton can be released for removal of the denture. The locking element supports itself thereby at the limit at a of the fixedly seated part, such that upon engaging and locking simultaneously the denture is slightly lifted. The locking element pushes again against this limit stops upon insertion of the denture and the locking element is thereby returned in its position, whereby the axis of the locking bar is released again.

On the one hand the high construction requirements based on the additional spring are a disadvantage in the solutions. On the other hand the locking mechanism is subject to interferences. If the denture is not seated completely free of friction at the fixedly seated part and the force of the second spring is insufficient to overcome this friction, then the locking mechanism fails.

A fully automatic bolting device has been proposed by the applicant in the German patent DE 197 28 863 C2, wherein a locking device is provided movably supported in the pushbutton or, respectively locking bar or in the casing, wherein the locking device releases the locking bar not upon insertion of the denture, as in case of the other fully automatic locking bars, but already upon removal of the denture. The described susceptibility to interference of the other fully automatic locking bars could thereby be eliminated. The expensive production of the locking bar device proved however to be a disadvantage.

SUMMARY OF THE INVENTION

1. Purpose of the Invention

It is the object of the present invention to generate an easily operatable denture attachment formed as a fully automatic locking bar, wherein the denture attachment operates without problems even in case of increased friction between removable denture and fixedly disposed part and which requires a comparatively small production expenditure.

2. Brief Description of the Invention

This object is accomplished by the connection element with the features of claim 1. The subclaims contain advantageous further embodiments of the connection element according to the present invention. In principle the known idea of a movably supported locking device from the German patent DE 197 28 863 C2 is taken up again with the present invention, wherein the locking device is placed into motion upon actuating of a pushbutton by the cooperation of limit stop and control faces. However the function of the locking device is here associated within easy lifting of the denture in contrast to the construction forms described in the German patent and similar as in case of the other fully automatic locking bars having become known. This spring force or the motion of a locking bar is deflected by way of limit stop and guide faces upon actuating of the pushbutton against the force of one or several springs such that the locking device moves. This motion in turn effects a slight lifting of the denture in pullout direction without limit stop at the fixedly seated part. Furthermore, the spring force can be deflected by limit stop and guide faces such that the spring force supports the denture in this slightly elevated position. This leads to constructions, wherein the release of the locking bar by the locking device does not occur during the removal of the denture as in case of the solutions of the German patent DE 197 28 863 C2, but only upon the insertion of the denture. The locking device retains the locking bar fixed against the force of the spring by the coaction of further limit stop faces. The same limit stop faces, which limit stop faces effect the lifting of the denture during the removal, effect the seating back of the locking device, wherein the locking device now again releases the locking bar. The spring can now return the locking bar such that the locking knowledge becomes effective.

Furthermore, modifications are possible, wherein in fact the locking device effects the lifting of the denture upon pressing of the pushbutton, wherein however the locking device is not held fixed itself. The locking bar nevertheless is initially however locked: based on the slight lifting of the denture the locking bar cannot any longer be led back into the corresponding undercut. The locking bar is the led back upon removal of the denture as in the constructions known from the German patent DE 19728863 C2, such that inclined faces have to be provided as described there, which inclined faces lead the locking bar against the force of the spring upon insertion of the denture.

A plurality of constructive solutions are conceivable for realizing the idea. Only several of the constructive possibilities are illustrated with reference to the drawings in more detail in the following. The individual elements presented in connection with the various described constructive possibilities can also be combined with each other.

BRIEF DESCRIPTION OF THE DRAWING

There is shown.

a FIG. 17 a horizontal central section along the locking bar longitudinal axis through a fifth connection element;

FIG. 18 a sectional view along the section line XVIII—XVIII through the connection element of FIG. 17;

FIG. 19 a sectional view along the section line XIX—XIX through the connection element of FIG. 17;

FIG. 20 a sectional view along the section line XX—XX through the connection element of FIG. 17;

FIG. 21 a sectional view along the section line XXI—XXI through the connection element of FIG. 17.

The sections are shown either vertical parallel relative to the locking bar longitudinal axis, horizontally parallel to the locking bar longitudinal axis or perpendicular to the locking bar longitudinal axis in all the drawings, wherein the locking bar longitudinal axis in all cases is disposed approximately perpendicular to the row of teeth and approximately parallel to the chewing surface. The pushbuttons D of the individual connection elements are placed in general on the side of the tongue for optical reasons.

DESCRIPTION OF INVENTION AND PREFERRED EMBODIMENT

Figure 1:
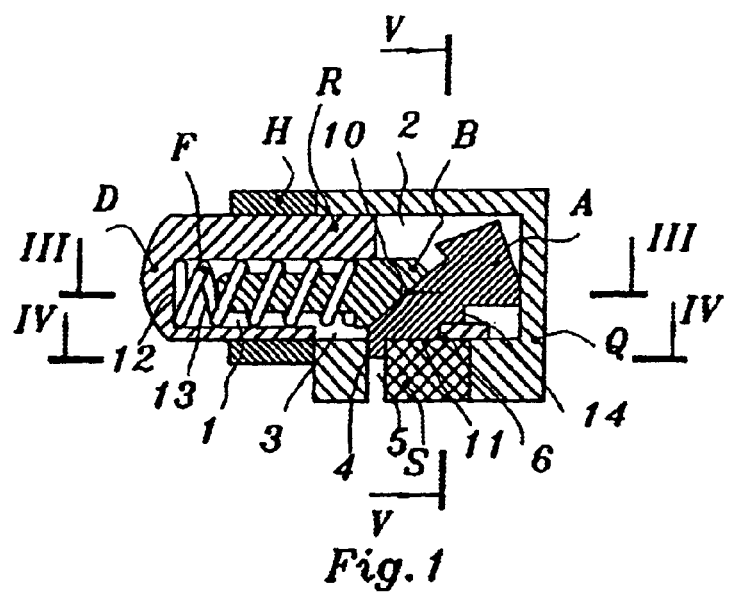
FIG. 1 a vertical central section along the locking bar longitudinal axis through a first connection element in locking position.

FIG. 1 shows a connection element with a box shaped casing G in locking position. A web extension or a web is designated with S, wherein the web extension or the web is formed at the tooth crown or, respectively at a tooth implant or also at several tooth crowns or tooth implants, that is fixedly attached in the oral cavity. An about cylindrically shaped locking bar R is supported slidingly along the longitudinal axis of the locking bar in the casing G. The guide of the locking bar outside of the casing in the area of the prosthetic body can be improved by a sleeve H. The locking bar R carries A pushbutton D, wherein the pushbutton D can be operated for debolting of the denture by the patient with the pulp. The plate shaped locking device A is such supported in the causing G that the plate shaped locking device essentially can perform only one motion perpendicular to the locking bar. A schematicly illustrated spring F is disposed in the locking bar R, wherein the spring F is supported through a bolt B, wherein the bolt B can be fixedly connected to the spring F, and through the locking device A in the casing G and thus the bolt B presses the locking bar R with the pusbutton D in the direction of the pushbutton D.

The spring F and the bolt B are guided in a suitable bore hole 1 of the locking bar R (FIGS. 1 through 3, FIG. 5). This bore hole is complemented in closing and basal direction by two slots 2 (FIGS. 1,2 and 5) and 3 (FIGS. 1 and 2), which slots 2 receive the locking device A. An extension 4 of the locking device A (FIGS. 1,2 and 4) is disposed in a corresponding recess 5 of the casing G (FIGS. 1 and 2) and thus secures the locking device A and the locking bar R against rotation. The locking bar R is furthermore secured against a falling out in the direction of the operation of the spring force by having the locking bar R pushing with a stop face 6 (FIGS. 1 and 2) against the locking device A, wherein the locking device A in turn is guided in this direction over the extension 4 in the recess 5 of the casing G.

Figure 12:
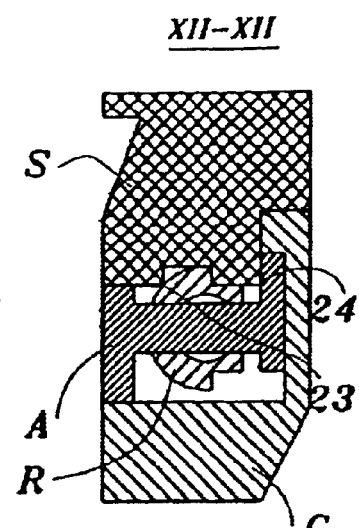
FIG. 12 a sectional view along the section line XII—XII through the connection element of FIG. 11.
Figure 13:
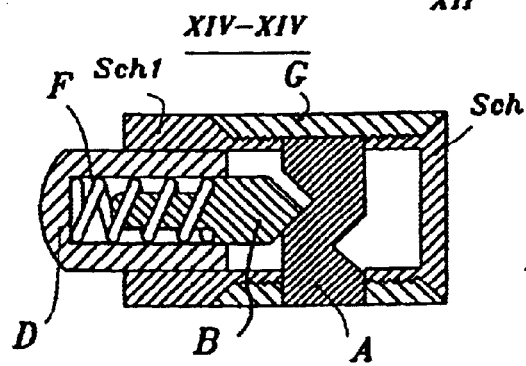
FIG. 13 a sectional view along the section line XIII—XIII through the connection element of FIG. 11.
Figure 14:
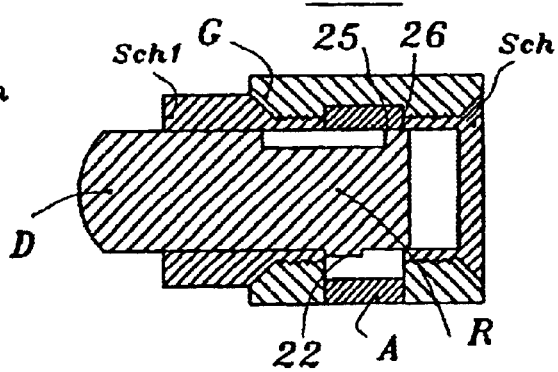
FIG. 14 a sectional view along the section line XIV—XIV through the connection element of FIG. 11.

The locking of the denture is effected by siding the locking bar R through the spring force with the parts 7 (FIGS. 3 and 5) effective for the bolting as seen from the an pullout direction of the denture under regions at the web extension 4, respectively, web S. The locking bar R rests here in a congruent bar eye 8 (FIG. 5) of the web extension or, respectively, of the web S. However, the web S does not have to show any recess congruent relative to the locking bar. It is decisive that the locking bar grips under regions of the fixedly seated part S. The locking bar is for example round according to FIG. 1, which however is not necessarily required. Connection elements with a different cross-sectional shapes are shown for example in the FIGS. 12 and

18. The round cross-sectional shape however is associated with advantages in production technology. On the other hand the locking effect can be improved by a corresponding cross-sectional shape. For example the effective parts of the locking bar R for the locking are enlarged in connection with the connection element of FIG. 18, and in case of the connection element according to FIG. 12 these parts grips under regions of the fixedly seated part S at least approximately at a right angle relative to the pullout direction.

Figure 2:
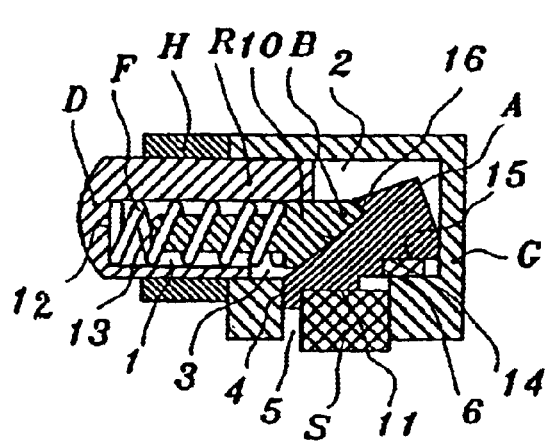
FIG. 2 a sectional view corresponding to FIG. 1 of the connection element in unbolted position.
Figure 3:
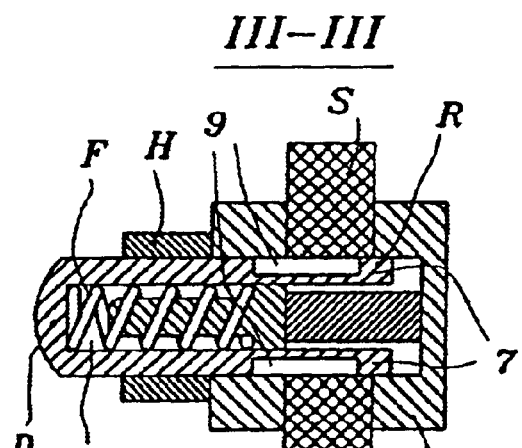
FIG. 3 a sectional view along the section line III—III through the connection element of FIG. 1.
Figure 4:
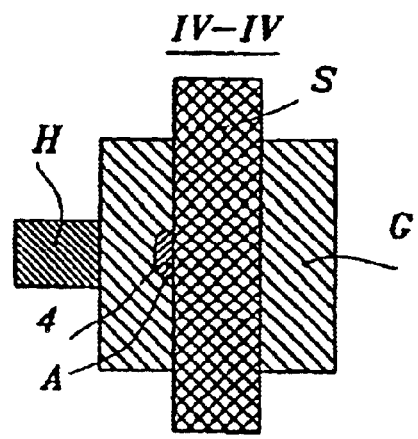
FIG. 4 a sectional view along the section line IV—IV through the connection element of FIG. 1.
Figure 5:
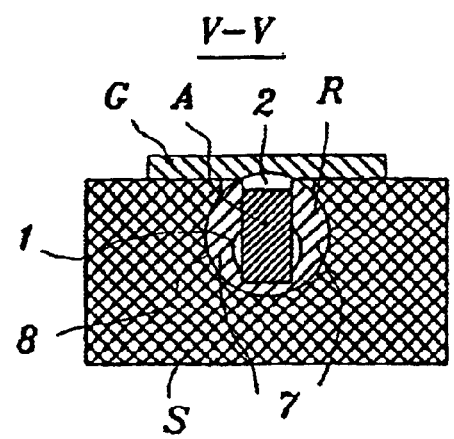
FIG. 5 a sectional view along the section line. V—V through the connection element of FIG. 1.

The patient pushes with the pulp onto the pushbutton D for removal of the denture. The locking bar R is thereby an shifted against the spring F, wherein the parts 7 (FIGS. 3 and 5) of the locking bar R effective for the locking are moved out of the undercut regions at the web extension or, respectively, the web S. The regions of the passage of the locking bar R only bar eye B (FIG. 5) is completely covered by the side flattenings 9 of the locking bar R (FIG. 3). The denture could now be removed as would be in case of a semi automatic locking bar. However the patient is to release the pushbutton D prior to removal of the dent re as in case of a completely automatic locking bar. Therefore the locking device has to become functioning. The spring F acts onto an inclined face 10 at the locking device A (FIGS. 1 and 2) through the bolt B. The locking device A rests with a basal limit stop face 11 (FIGS. 1 and 2) at the base of the bar eye 8. Since the construction is now unlocked, the spring force can move the locking device A relative to the casing G and to the locking bar R to some extent in basal direction and based on the resting of the locking device A at the base of the bar eye 8, that is at the fixedly seated part, the spring force can lift the complete connection element and thus the denture to some extent in closing direction. If the friction between the different components is larger than the spring force, then the slight lifting of the connection element is assured, by a further pressing of the pushbutton D. The locking bar R pushes then with a limit stop 12 against a limit stop 13 at the bolt B (FIGS. 1 and 2), whereby the bolt B is moved together with the locking bar R. The lifting of the connection element is effected through the inclined face 10 at the locking device A as as well as the basal limit stop face 11 at the locking device A (FIG. 12) and their resting at the base of the bar eye 8. The limit stop face 6 of the locking bar R comes now to lie behind the limit stop face 14 of the locking device A based on the relative motion off the locking device A in basal direction as shown in FIG. 2. A leading back of the locking bar R with the pushbutton D through the spring F is thus prevented, the locking bar is locked. The locking device. A is held in this position shifted in basal direction by the force of this spring F, wherein the force on the spring F operates onto the inclined face 10 of the locking devise through the bolt B. The pushbutton D can now be released for removal of the denture.

The basal motion of the locking device A will not be a pure parallel shifting based on the unavoidable play between the device components and based on the geometry of the locking device A. Obviously, the basal motion will initially at the side disposed toward the bolt B flip somewhat in basal direction prior to the shifting in basal direction. In case of a sufficiently precise production of the parts this effect does not have such strong consequences that the functioning of the connection element is interfeed with. An improved parallel shifting of the locking device A can be achieved by allowing a pin to protrude from the side disposed away from the pushbutton D of the casing G into the bore hole 1 of the locking bar (FIGS. 1 through 3, FIG. 5) up to close at the bolt B, wherein the correspondingly shorter formed locking device A is led at the bolt B in basal direction. The locking device A thereby becomes however more inconvenient. In addition the construction expenditure for the casing G is increased.

As illustrated, the locking device A can be moved in basal direction by the effect of the force of this spring F or based on the motion of the locking bar R. Similarly constructions are possible, wherein only one of these effects is employed. The transfer of the motion of the locking bar in a basal motion of the locking device A can occur instead of bolt B also by stop face directly attached on to the locking bar.

The holding of the locking device in a position shifted in basal direction can also be effected by having the limit stop faces 6 and 14 (FIGS. 1 and 2) formed not exactly perpendicular to the direction of motion of the locking bar R, but somewhat inclined thereto, wherein the faces are disposed at their closing end closer to the pushbutton D than at their basal end. Such a solution was elected in the connection element illustrated in FIG. 1 and is described in more detail below.

The locking device A is secured against following out in basal direction by being seated in its position shifted in a basal direction with a limit stop face 15 in the locking bar R as well as by pushing with a limit stop face 16 against the bolt B (FIG. 2). However, there are also other possibilities to secure the locking device A the against falling out in a basal direction. For example also a basal limit stop can be furnished in front of the recess 5 of the casing G as seen from the pushbutton D instead of the limit stop face 16. This basal limit stop can also be placed in the recess 5 by closing the recess 5 below the extension 4 of the locking device A.

During insertion of the denture the locking device A impinges with its basal limit 3top face 11 (FIGS. 1 and 2) onto its support at the base of the bar eye 8 and is thereby again somewhat moved relative to the casing G and to the locking bar R in closing direction. The limit stop 14 of the locking device A now releases again the limit stop 6 of the locking bar R, such that the spring F can lead back again the locking bar R with the pushbutton D. The denture is now locked.

Figure 15:
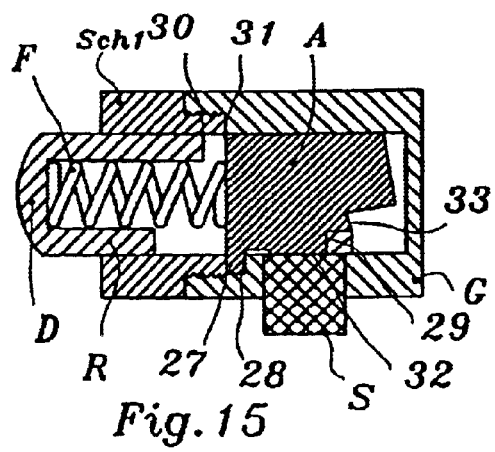
FIG. 15 a vertical central section along the locking bar longitudinal axis through a third connection element.

A demounting of the movable parts for exchange and repair purposes is easily possible. The locking device A is pressed in the region of the basal face 11 in closing direction with a fine instrument, wherein initially the bolt B is moved against the spring F. The locking device A is thereby somewhat rotated The locking device A is thereby somewhat rotated, since the locking device A pushes with its side disposed remote from the bolt B on the top in the casing G. As soon as the extension 4 is moved out of the corresponding recess 5 of the casing G, then the locking bar R together with the spring F, the bolt B and the locking device A can be pulled out. Also analogous constructions with sleeve shaped screw, as illustrated in the connection elements of FIGS. 11 and 15, or with a basally inserted screw as in the connection element of FIG. 15 are possible, wherein then a demounting can be performed after removal of the screw.

Figure 6:
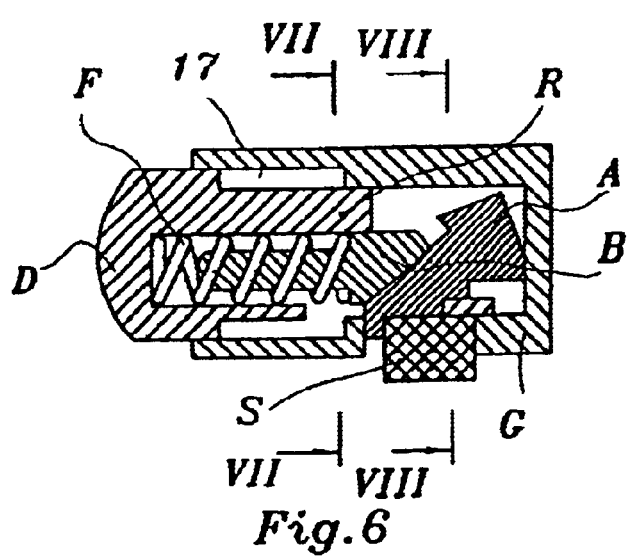
FIG. 6 a vertical central section along the locking bar longitudinal axis through a modified form of the connection element of FIG. 1.
Figure 7:
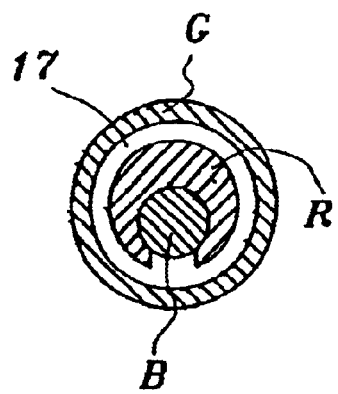
FIG. 7 a sectional view along the section line VII—VII through the connection element of FIG. 6.
Figure 8:
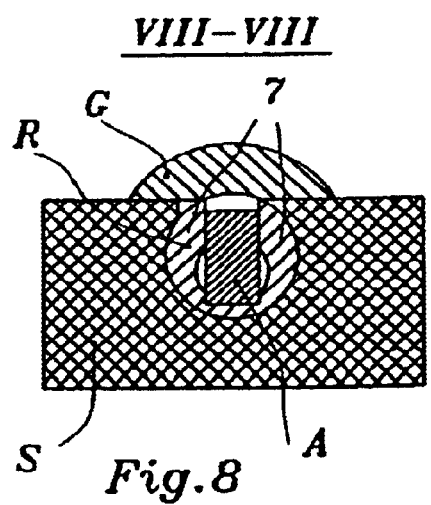
FIG. 8 a sectional view along the section line VIII—VIII through the connection element of FIG. 6.

A modification of the described connection element is shown in FIGS. 6 through 8, which modification functionally corresponds to this connection element, however is distinguished by the shape of the casing G. The casing G is here formed sleeve shaped. This casing can be formed short in the direction of the locking bar longitudinal axis such that then again an additional sleeve H can be incorporated in the denture body for guiding the locking bar R. The casing G can also be constructed long, as illustrated here, such that the additional sleeve H can be dispensed with. As shown here, the pushbutton D can be formed with a larger diameter as the balance of the locking bar R for a better possibility of operation. A further spring acting like the spring F could be inserted into the hollow space 17 (FIGS. 6,7) between the locking bar R and the casing G for improving of the spring function. Constructions are also possible, wherein the spring is disposed completely outside of the locking bar. The locking bar R engages here with its parts 7 (FIG. 8) effective for the locking on two sides in under cuts at the web extension or web S.

Figure 9:
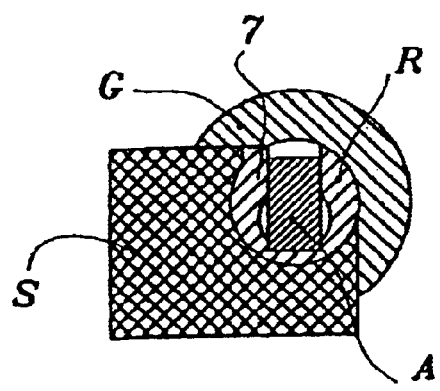
FIG. 9 a sectional view corresponding to FIG. 8 perpendicular to the locking bar longitudinal axis of a further modification of the connection element of FIG. 1.
Figure 10:
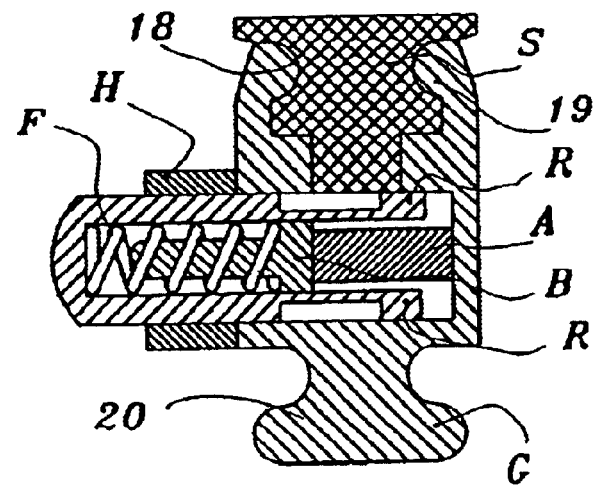
FIG. 10 a horizontal central section along the locking bar longitudinal axis through a further modification an of the connection element of FIG. 1.

FIG. 9 shows a modification of these sleeve shaped casing form, wherein the locking bar R with its effective parts 7 engages only on one side into the web extension S. FIG. 10 shows an application at the web extension with again a one-sided engagement Of the effective locking bar parts 7, wherein the web extension exhibits here half round shown guide grooves 18 for improving the guiding function during insertion of the denture. Either parts of the denture frame or—as shown here—guiding parts 19 of the casing G can engage into these guiding grooves. The casing G carries a dove tail like extension 20, wherein the dove tail like extension 20 improves in particular in case of adhesive technology the connection between the connection element and the denture frame. It is necessary with this construction to provide two different versions of the casing G for right side and for left side application. The possibility exists also perform the casing of two parts, wherein the second sleeve shaped casing part, which casing part looks similar as the shown in FIG. 9, is insertable on two sides into a box shaped first casing part, where the first casing part is seated on the web extension, for avoiding of the two recited versions for two side application. A special form of the casing can be constructed for the interdental application between two telescope crowns. The special form then has to be formed extremely narrow.

Figure 11:
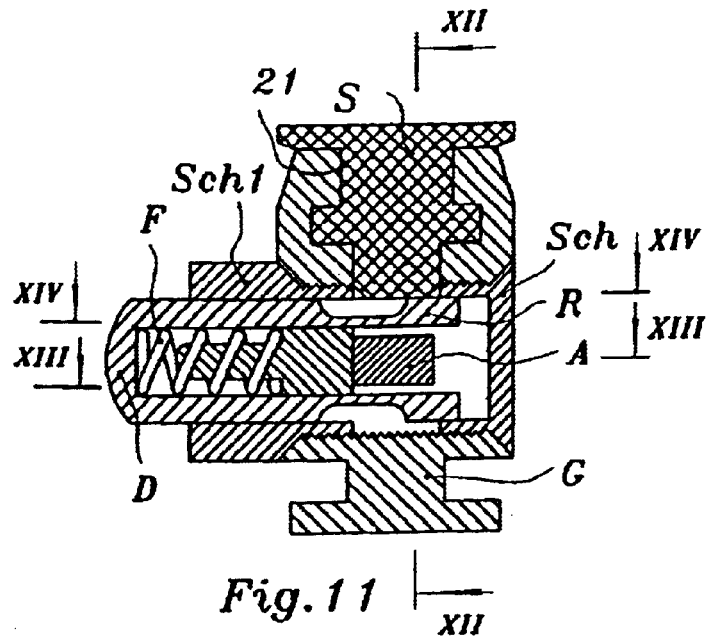
FIG. 11 a horizontal central section along the locking bar longitudinal axis through a second connection element.

A second connection element is shown in FIGS. 11 through 14. A casing G is seated onto a web extension S, wherein the web extension S can exhibits angular illustrated guide grooves 21 (FIG. 11). A sleeve shaped screw Sch1 can be inserted on two sides in this casing G, wherein the locking bar R with the pushbutton D is guided in the sleeve shaped screw Sch1, wherein the locking bar R is secured against falling out by an extension 22 (FIG. 14) and a disassembly can be easily performed after removing of the screw Sch1. The opening disposed opposite to the screw Sch1 can be closed by a screw Sch. All construction parts are formed such that they can be applied on both sides. A locking device A is supported slidable in vertical direction in the casing G. The locking bar R grips with its effective parts 23 for the locking, wherein the effective parts 23 here form a face disposed vertical to the pullout direction, on one side (FIG. 12) the undercut regions at the web extension. The function of the spring F, of the bolt B, and of the locking device A corresponds essentially to the corresponding elements in the connection element illustrated further above. The locking device A with its limit stop face 24 rests however at the top at the web extension S (FIG. 12) in contrast to the further above illustrated connection element. This support effect s a slight lifting of the connection element upon actuation of the pushbutton D. The locking device A effects then the locking of the locking bar R with the limit stop face 26 of the locking device A (FIG. 14), wherein the locking bar R pushes with its limit stop face 25 (FIG. 14) against the limit stop face 26.

The locking device A with a basal extension 27 is such supported in a basal recess of the casing G that the locking device A is rotatable around an axis 28 disposed perpendicular to the longitudinal axis of the locking bar R and rotation of the locking bar R around its longitudinal axis is not possible, in connection with the connection element illustrated in FIG. 15, wherein the locking device A is disposed within slots of the locking bar R. A sleeve shaped screw Sch1 secures the locking device A and thus also the locking bar R against falling out, since the locking bar R pushes with a limit stop 29 against the locking device A. The spring F, which spring F can also be solidly connected to the locking device A, set at the locking device A effects a rotation of the locking device A around the rotation axis 28 away from the pushbutton D upon actuation of the pushbutton D. A limit stop face 30 effects the same, wherein the limit stop face 30 also pushes against a limit stop 31 of the locking device A upon further pressing of the pushbutton d. A basal limit stop face 32 of the locking device A rests at the bottom at the web extension or web S and effects a slight lifting of the connection elements based on the rotation as with the connection element illustrated in FIGS. 1 through 5, wherein then the locking bar R with the limit stop 29 pushes against a limit stop face 33 of the locking device A and is thus locked. The limit stop face 32 of the locking device A pushes against the web extension or, respectively web S upon reentering of the denture and becomes thereby turned back and releases again the locking bar.

Figure 16:
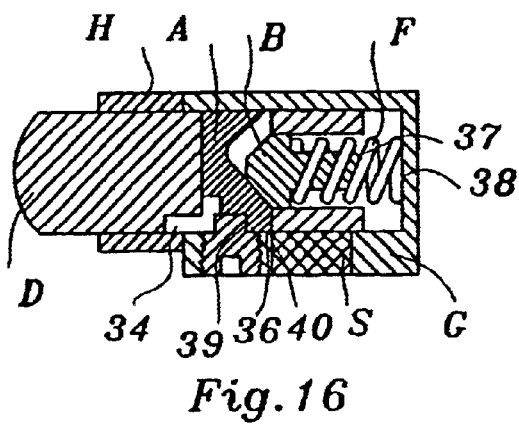
FIG. 16 a vertical central section along the locking bar longitudinal axis through a fourth connection element.

The locking device A in contrast to the up to now described locking elements is not disposed in the casing G, but instead slidingly supported in a vertical direction in the locking bar R according to the connection element shown in FIG. 16. A screw Sch2 protruding from a basal direction into a groove 34 of the locking bar R secures the locking bar R against falling out and against rotation. The locking device A is moved against the bolt B subjected to the spring F upon actuation of the pushbutton D. The spring force effects a slight basal motion of the locking device A relative to the casing G through the bolt B and an inclined face 35 at the locking device A. Since the locking device A then rests with a basal limit stop face 36 at the web extension or web S, a slight lifting of the connection element in pullout direction occurs. If the spring force is insufficient for releasing this motion, then the same is released by a pushing of the bolt B with a limit stop face 37 at a belonging limit stop 38 of the casing G upon further pressing of the pushbutton D. The locking of the locking bar R is effected by having the locking device A with a limit stop face 39 pushed against a limit stop face 40 of the casing G. The connecting element is easily held in the slightly lifted position by the spring force, which spring force operates onto the inclined face 35 of the locking device A through the bolt B. The locking device A is pushed upwardly by the web extension or, respectively, web S through the basal limit stop face 36 of the locking device A during reinsertion of the denture and the locking device A releases again the locking bar R.

A completely different construction of connection element is shown in FIGS. 17 through 21. A casing composed out of two parts G1 and G2 for production technological reasons is seated on a web extension or web S. A sleeve H is inserted into the casing and is secured (FIG. 19) by a basal screw Sch3, wherein the basal screw can be removed for disassembly purposes. A locking bar R is supported slidable along the longitudinal axis of the locking bar and limited rotatable around the longitudinal axis of the locking bar in the sleeve H and in the casing part G2. A pushbutton D is placed on the locking bar R, wherein the connection between the two parts can be performed by press fitting, bolting or screwing together. As spring A disposed around the locking bar R acts against the pushbutton D. The locking bar R engages on two sides in undercut regions at the web extension or web S (FIGS. 17 and 18) with side extensions 41 and 42 of the locking bar R effective for the locking. The extension 42 with an inclined to limit stop face 43 pushes against a limit stop face 44 of the casing part G2 (FIG. 20) in case of pressure onto the pushbutton D, wherein the locking bar R is placed into rotation around its longitudinal axis. Since the same extension 42 rests with a basal limit stop face 45 (FIG. 20) on the web extension or web S, the connection element is lifted slightly in pullout direction. Upon releasing the pushbutton D, the spring F places initially the locking bar R somewhat backward. A further leading back of the locking bar is however prevented by having the extension 41 with the limit stop 46 pushed against a limit stop 47 of the sleeve H (FIG. 21) based on the rotation of the locking bar. The faces 46 and 47 are disposed not precisely rectangular relative to the direction of motion of the locking bar R. The faces 46 and 47 are disposed in closing direction closer to the pushbutton B as compared in basal direction. This is associated with the consequence that the spring force acting in the direction of the pushbutton D retains the locking bar R and thus the connection element in this position. The extensions 41 and 42 thus cooperate as locking device A. The pushbutton D can now be released for removal of the denture. The locking bar R rotates backward upon reinsertion of the denture based on the beating of the basal limit stop face 45 at the web extension or web S. The spring F can now lead back the locking bar R into the bolting position.

Slight changes by not illustrated constructive modifications are possible relative to the described constructions, where the locking device A in fact slightly lifts the connection element upon pressing of the pushbutton D, wherein the locking of the locking bar R by the locking device A itself is however dispensed with. Indirectly, the locking device A initially nevertheless locks the locking bar R here. The locking bar cannot be set back any longer into the associated undercuts based on the slight lifting of the denture. Upon removal of the denture the locking bar is however lead back by the spring F such that inclined faces have to be provided, wherein the inclined faces guide the locking bar R upon insertion of the denture against the force of the spring F.

The component parts can advantageously be produced as packaging parts and for example being made out of a dental alloy. The spring can be produced out of a suitable spring material, for example a stainless-steel or a suitable titanium alloy. The spring can comprise out of an elastic plastic body upon a corresponding modification of the construction. The locking bar head of the connection element illustrated in FIGS. 17 through 21 can be made out of plastic, similarly the sleeves of the connection elements of the FIGS. 1 through 5 and 10 and 16. They can be polymerized into the denture. The web extension or web can be made out of a bakable plastic and is cast together with the remaining fixed seated constructions. Furthermore the web extension or web can comprise an extension gate capable alloy. The casing is attached for example by adhesive attachment, by welding or soldering in the denture frame, wherein preferably the adhesive technology or the laser welding should be applied for biological reasons. A suitable recess for the connection element has to be created in the denture frame. For this purpose doubling auxiliary parts made out of plastic or metal or auxiliary parts made out of ceramics can be employed.

A special shape of the invention comprises that the casing G is dispensed with and the guide for the locking bar R and the remaining recesses of the casing G are produced directly in the denture frame. For example the recesses for an the locking bar R and for the screw Sch2 can be produced by drilling in the connection element illustrated in FIG. 16, wherein the position of the bore holes relative to each other could be fixed with a drilling jig. In the following a threat would have to be cut into the bore hole for the screw Sch2. The passage of the locking bar R through the web extension or web S could be produced together with its guiding in the denture frame. Another possibility of the production of the recesses is a spark erosion. Furthermore for example an auxiliary part out of ceramics could be modeled into the denture frame for the guiding of the locking bar R as well as the recess 5 of the extension for in the connection element illustrated in FIGS. 1 through 10, wherein the auxiliary part could be easily removed by emission out of the denture frame after the casting. This auxiliary part can also be produced out of a high melting metal, for example nickel, which can be dissolved with a suitable acid, for example, nitric acid after the casting.

The locking bar can also be offered in a semi automatic version by slight changes. For example, the locking device A can be modified such, that the stop face 16 (FIG. 2) already rests on the bolt B in locking position and thus a shifting of the locking device in basal direction on is not possible.

If an inner thread is placed into the guide of the locking bar R, then a screw can be employed instead of the locking bar, wherein the screw is formed cylindrically with the same diameter as the locking bar at the end of the screw disposed remote from the screw head. A fixed connection between the fixedly seated part and the secondary part carrying the screw can be produced by insertion of the screw. This makes sense for example in the case where the secondary part is a fixedly seated on bridge piers, which bridge piers however exhibit long-term a doubtful prognosis. After loss of these bridge piers the construction can be reconstructed easily into a removable denture by engaging of the screw connection and by inserting a locking bar instead of the screw.

What is claimed is:

1. A connection element for the attachment of removable tooth dentures to crowns oil teeth or tooth implants comprising
   a fixedly seated element (S) connected to a tooth crown or a tooth implant;
   a locking device (A) to be placed on the fixedly seated element (S) and having a first limit stop face and having a second limit stop face (14);
   a spring (F) a locking bar (R) supported slidable in a first direction and having a third limit stop face (6) and a third limit stop plane (15), wherein the third limit stop face (6), wherein the third limit stop face (6) is alternatively engageable with the first limit stop face and with the second limit stop face (14) and wherein the locking bar (R) is supported by the force of the spring (F);
   a pushbutton (D) acting upon the locking bar (R), wherein the third limit stop face (6) of the locking bar (R) is engaged with the second limit stop face (14) when the pushbutton (D) is depressed, wherein the third limit stop face (6) remains engaged with the second limit stop face (14) upon release of the push button (D), and wherein the third limit stop face (6) becomes engaged with the first limit stop face upon placing of the locking device (A) onto the fixedly seated element (S), and
   wherein the locking device (A) is movable upon actuation of the pushbutton (D) in the direction of the third limit stop face (6) engaging the second limit stop face (14) against a force of the spring (F) such that the spring (F), the locking bar (R) and the pushbutton (D) become slightly lifted in a removal direction of the denture disposed substantially perpendicular to the first direction.

2. A connection element for the attachment of removable tooth dentures to crowns of teeth or tooth implants, comprising a locking bar (R) carrying a pushbutton (D), wherein the locking bar (R) is supported slidable in a first direction, and wherein the locking bar (R) comprises a bore hole (1) and parts (7) with a side flattenings (9), and wherein the parts (7) comprise a limit stop (6), a spring (F) disposed inside the locking bar (R), a bolt (B) having a side disposed at the spring (F) and an opposite side with an inclined face, wherein the spring (F) and the bolt (B) are guided in the bore hole (1) of the locking bar (R), a locking device (A) shaped like a plate and surrounding the bolt (B) and having an extension (4) and an inclined face engaging with the inclined face of the bolt (B), a casing (G) shaped like a box and having a recess (5) and a bar eye (8), wherein the casing (G) contains the locking bar (R) with the pushbutton (D), the spring (F), the bolt (B) and the locking device (A), and wherein the casing (G) is attachable at a fixedly seated element (S) connected to a tooth crown or a tooth implant, and wherein the locking device (A) is supported in the casing (G) that the locking device (A) essentially can perform a motion in a second direction disposed perpendicular to the first direction, wherein the extension (4) of the locking device (A) is disposed in the recess (5) of the casing (G) and thus secures the locking device (A) and the locking bar (R) against rotation, wherein the locking bar (R) is guided inside the casing (G), wherein the parts (7) of the locking bar (R) are disposed between the locking device (A) and the fixedly seated element (S) and wherein the locking bar (R) together with the parts (7) move in the first direction upon a pushing of the pushbutton (D) in order to cover the bar eye (8) completely by the side flattenings (9) of the locking bar (R), and wherein the limit stop (6) of the locking bar (R) moves from the limit stop face (101) to the limit stop (14) releasing the locking device (A) before the spring (F) is compressed, and wherein after the spring (F) is compressed, the pushbutton (D) transfers horizontal motion to the bolt (B), and wherein the bolt (B) pushes the locking device (A) in the second direction toward the fixedly seated element (S), and wherein the casing (G) with the locking bar (R), with the spring (F), with the bolt (B) and with the locking device (A) is removed away from the fixedly seated element (S), and wherein the limit stop face (6) of the locking bar (R) engages the limit stop (14).

3. The connection element according to claim 2 wherein the pushbutton (D) transfers motion in the first direction to the bolt (B) upon compressing the spring (F);

wherein the locking device (A) includes a basal limit stop face (11) and a second limit stop face (14);

wherein the parts (7) of the locking bar (R) are disposed between the locking device (A) and the fixedly seated element (S);

wherein a third limit stop face (6) of the locking bar (R) moves from a first limit stop face (101) to a second limit stop face (14) for releasing the locking device (A);

wherein the bolt (B) moving in the first direction pushes the locking device (A) in the second direction toward the fixedly seated element (S).

4. A connection element for the attachment of removable tooth dentures to a support, comprising a casing (G), a locking device (A) disposed in the casing (G) and slidable in a defined direction and having an extension, and having a first limit stop face (101), and a second limit stop face (14) and to be seated on a fixedly seated element (S) between the extension and a wall of the casing (G) and having an inclined face (10);

a spring (F);

a bolt (B) supported by the spring (F) and having a counter-inclined face engaging the inclined face (10) under pressure of the spring (F) while the locking device (A) locks tight to the fixedly seated element (S);

a locking bar (R) movable in a first direction disposed at an angle to the second direction and supported by the spring (F) and having a third limit stop face (6) engaging the second limit stop face (14) when the locking bar (R) is pressed against the spring force for releasing the locking device (A) and for the locking bar (R) releasing the fixedly seated element (S).

5. The connection element according to claim 4 wherein the locking bar (R) comprises a pushbutton (D), a bore hole (1) and parts (7) having a side flattenings (9);

and wherein the parts (7) are disposed between the locking device (A) and a fixedly seated element (S);

and wherein the third limit stop face (6) contacts the first limit stop face (101) during locking, and wherein the locking bar (R) is supported slidable in the first direction.

6. The connection element according to claim 4 wherein the casing (G) comprises a recess (5) and a bar eye (8), wherein the locking bar (R) is guided inside the bar eye (8) of the casing (G);

and wherein the casing (G) is attachable in the first direction at the fixedly seated element (S);

and wherein the locking device (A) is supported in the locking bar (R) and wherein the locking device (A) essentially performs a motion only in the second direction;

wherein the extension (4) of the locking device (A) is disposed in the recess (5) of the casing (G) and thereby secures the locking device (A) and the locking bar (R) against rotation.

7. The connection element according to claim 4 wherein upon pushing of the pushbutton (D), the locking bar (R) together with the parts (7) and with the third limit stop (6) move in the first direction from the first limit stop face (101) to the second limit stop face (14) and removing parts (7) disposed in a way of removing the locking bar (R) from the fixedly seated element (S) in order to allow the locking bar (R) to slide out of the bar eye (8) completely through side flattenings (9) of the locking bar (R).

8. The connection element according to claim 4 wherein the bolt (B) comprises a first end disposed in the area of the pushbutton (D) and a second end carrying a counter-inclined face, wherein the spring (F) and the bolt (B) are guided in a bore hole (1) of the locking bar (R);

and wherein the pushbutton (D) upon a compressing of the spring (F) transfers motion in the first direction to the bolt (B).

9. The connection element according to claim 4 wherein the locking device (A) is plate-shaped, and wherein the locking device (A) surrounds the bolt (B), and wherein the locking device (A) comprises an inclined face engaging to the counter-inclined face of the bolt (B), and wherein the bolt (B) pushes the locking device (A) in the second direction;

and wherein the casing (G) with the flocking bar (R), with the spring (F), with the bolt (B) and with the locking device (A) is pulled out in the second direction from the fixedly seated element (S) of the support.

10. A connection element for the attachment of removable tooth dentures to crowns of teeth or tooth implants comprising a fixedly seated element (S) connected to a tooth crown or a tooth implant;

a spring (F) having a first end and having a second end;

a locking bar (R) supported slidable in a first direction, wherein the locking bar (R) locks the fixedly seated element (S) in a locked position to the locking bar (R) and wherein the locking bar (R) unlocks the fixedly seated element in a removal position from the locking bar (R);

a pushbutton (D) supported by the force of the first end of the spring (F) and acting upon the locking bar (R), wherein pressing of the pushbutton (D) initially presses on the first end of the spring (F);

a bolt (B) having a first end facing the pusbutton (D) and having a second end furnishing a counter-inclined faced, wherein the bolt (B) is supported by the force of the second end of the spring (F), and wherein, after compression of the spring (F), the said first end of the bolt (B) is being acted upon directly by the pusbutton (D) and wherein the bolt (B) is disposed slidably in the locking bar (R);

a locking device (A) having a locked position relative to the seated element (S) and having a removal position relative to the fixedly seated element (S) for allowing separation of the locking device (A) from the fixedly seated element (S) and having an inclined face (10) for facing the counter-inclined face of the bolt (B) such that a pressing of the pushbutton (D) induces a pressing of the counter-inclined face of the bolt (B) onto the inclined face (10) of the locking device (A) which in turn induces a shifting of the locking device (A) away from the locking bar (R) in a second direction perpendicular to the first direction and places the locking device (A) and the locking bar (R) into the removal position;

and wherein a pressing of the locking bar (R) in the second direction toward the fixedly seated element (S) induces the inclined face (10) of the locking device (A) to press against the counter-inclined face of the bolt (B) and in turn induces the locking device (A) and the locking bar (R) to move into the locking position.

11. A method for an attachment of removable tooth dentures to crowns of teeth or tooth implants comprising connecting a fixedly seated element (S) to a tooth crown or a tooth implant;

furnishing a locking device (A) to be placed on the fixedly seated element (S) and having a first limit stop face (101) and having a second limit stop face (14) and having a first limit stop lane (111) and having a second limit stop plane (114); placing a spring (F) into a locking bar (R) supported slidable in a first direction and having a third limit stop face (6) and having a third limit stop plane (15), wherein the third limit stop face (6) is alternatively engageable with the first limit stop face (101) and with the second limit stop face (14) and wherein the third limit stop plane (15) is alternatively engageable with the first limit stop plane (111) and with the second limit stop plane (114);

engaging the locking bar (R) with the flocking device (A);

supporting a pushbutton (D) by the force of the spring (F);

pushing the pushbutton upon the locking bar (R) for first moving the locking bar R in a first direction from a neighboring position of the third limit stop face (6) of the locking bar (R) and the first limit stop face (101) of the locking device (A) and from a neighboring position of the third limit stop plane (15) of the locking bar (R) and the first limit stop plane (111) of the locking device (A);

moving the locking device (A) in a second direction disposed perpendicular to the first direction to a neighboring position of the third limit stop face (6) of the locking bar (R) and the second limit stop face (14) of the locking device (A) and to a neighboring position of the third limit stop plane (15) of the locking bar (R) and the second limit stop plane (114) of the locking device (A);

removing the locking bar (R), the locking device (A), the pushbutton (D), and the spring (F) from the fixedly seated element (S).

12. The method according to claim 11 further comprising pressing the locking bar (R), the locking device (A), the pushbutton (D), and the spring (F) against the fixedly seated element (S);

moving the locking device (A) in the second direction from a neighboring position of the third limit stop face (6) of the locking bar (R) and the second limit stop face (14) of the locking device (A) and from a neighboring position of the third limit stop plane (15) of the locking bar (R) and the second limit stop plane (114) of the locking device (A);

moving the locking bar R in the first direction to a neighboring position of the third limit stop face (6) of the locking bar (R) and the first limit stop face (101) of the locking device (A) and to a neighboring position of the third limit stop plane (15) of the locking bar (R) and the first limit stop plane (111) of the locking device (A).

13. A method of using removable tooth dentures comprising connecting a fixedly seated element (S) to a tooth crown or a tooth implant;

furnishing a locking device (A) to be placed on the fixedly seated element (S) and having a first limit stop face (101) and having a second limit stop face (14) and having a first limit stop plane (111) and having a second limit stop plane (114);

placing a spring (F) into a locking bar (R) supported slidable in a first direction and having a third limit stop face (6) and having a third limit stop plane (15), wherein the locking bar (R), the locking device (A), and the spring (S) form a connecting piece;

moving the locking bar (R) in a first direction from a neighboring position of the third limit stop face (6) of the locking bar (R) and the first limit stop face (101) of the locking device (A) and from a neighboring position of the third limit stop plane (15) of the locking bar (R) and the first limit stop plane (111) of the locking device (A);

moving the locking device (A) in a second direction disposed perpendicular to the first direction to a neighboring position of the third limit stop face (6) of the locking bar (R) and the second limit stop face (14) of the locking device (A) and to a neighboring position of the third limit stop plane (15) of the locking bar (R) and the second limit stop plane (114) of the locking device (A);

removing the connecting piece from the fixedly seating element (S);

pressing the connecting piece against the fixedly seated element (S);

moving the locking device (A) in the second direction from a neighboring position of the third limit stop face (6) of the locking bar (R) and the second limit stop face (14) of the locking device (A) and from a neighboring position of the third limit stop plane (15) of the locking bar (R) and the second limit stop plane (114) of the locking device (A);

moving the locking bar R in the first direction to a neighboring position of the third limit stop face (6) of the locking bar (R) and the first limit stop face (101) of the locking device (A) and to a neighboring position of the third limit stop plane (15) of the locking bar (R) and the first limit stop plane (111) of the locking device (A).

* * * * *